(12) United States Patent
Garfinkel

(10) Patent No.: US 6,382,974 B1
(45) Date of Patent: May 7, 2002

(54) CURETTE FOR DEEP POCKET PERIODONTAL CURETTAGE

(76) Inventor: Leonard M. Garfinkel, 3050 N. 35th St., Hollywood, FL (US) 33021

(*) Notice: Subject to any disclaimer, the term of this patent is extended or adjusted under 35 U.S.C. 154(b) by 0 days.

(21) Appl. No.: 09/848,926

(22) Filed: May 3, 2001

(51) Int. Cl.[7] ................................. A61C 3/02
(52) U.S. Cl. ........................... 433/144; 433/141
(58) Field of Search ....................... 433/141, 142, 433/143, 144

(56) References Cited

U.S. PATENT DOCUMENTS

| | | | | |
|---|---|---|---|---|
| 1,138,355 A | * | 5/1915 | Carr | 433/143 |
| D53,958 S | * | 10/1919 | Zurbrigg | 433/142 X |
| 1,605,320 A | * | 11/1926 | Bates | 433/144 X |
| 1,605,322 A | * | 11/1926 | Bates | 433/144 |
| 2,154,751 A | * | 4/1939 | Hoskins | 433/144 |
| 4,505,678 A | * | 3/1985 | Andersson | 433/143 |

* cited by examiner

*Primary Examiner*—Nicholas D. Lucchesi
(74) *Attorney, Agent, or Firm*—Malin, Haley & DiMaggio, P.A.

(57) ABSTRACT

This invention relates to a periodontal instrument and curettage method for separating and removing calculus and diseased granulation tissue from the tooth surface and periodontal cavity in deep pockets greater than 10 mm. The invention is comprised of a straight shaft, a distal portion in parallel orientation with and terminating in a spoon-shaped blade with a rounded tip and continuous sharp edge. The approximate 90 degree angle orientation between the distal and proximal shank portions, rounded blade tip, and parallel alignment of the blade face relative to the distal shank portion enhance maneuverability, accessibility, and efficiency and minimize tissue trauma during periodontal curettage.

1 Claim, 3 Drawing Sheets

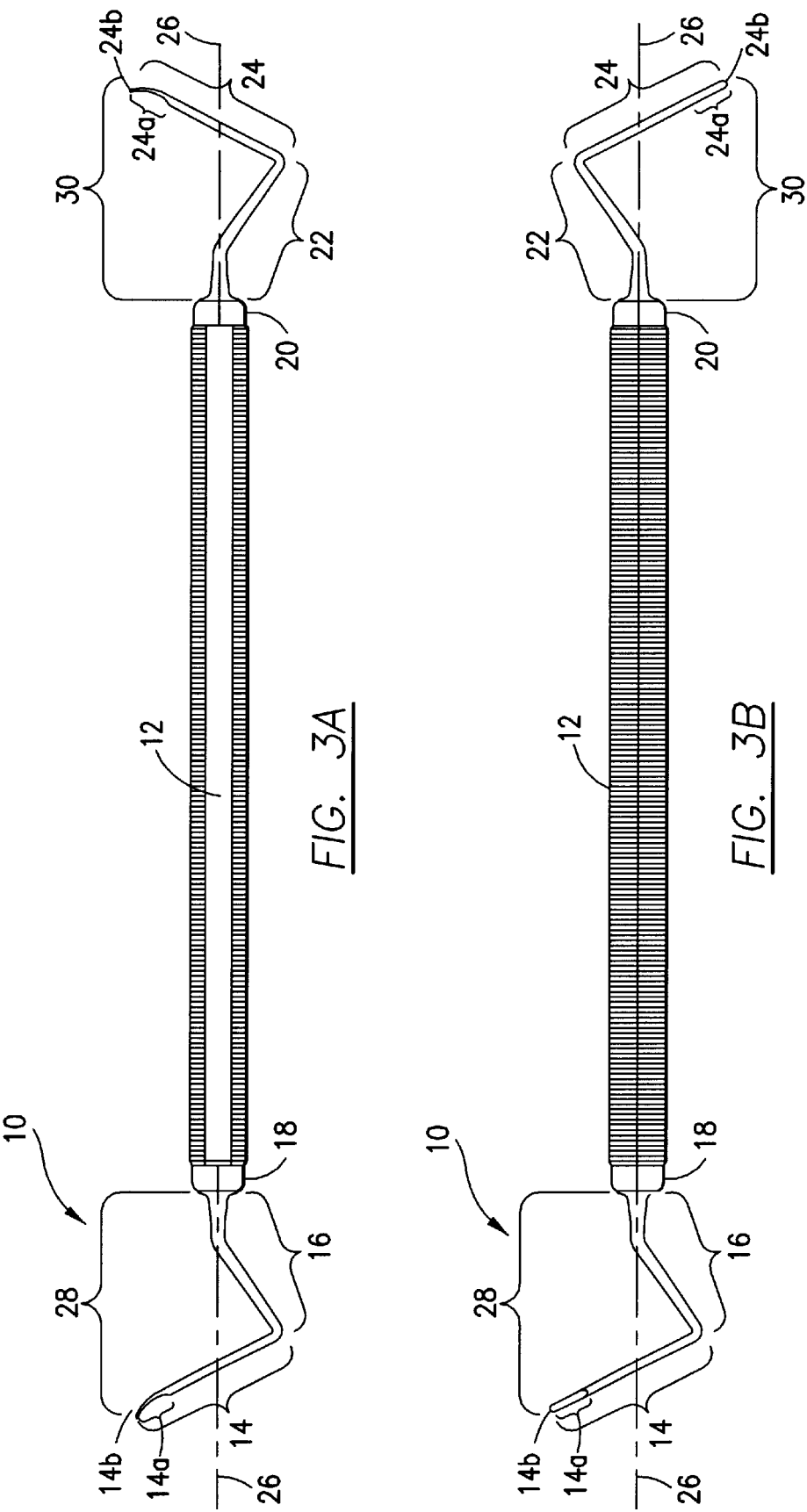

CURETTE FOR DEEP POCKET PERIODONTAL CURETTAGE

BACKGROUND OF THE INVENTION

1. Field of the Invention

The present invention relates to dental tools and more particularly to a periodontal curette for removal of diseased tissue and calculus from bottom areas of deep periodontal pockets.

2. Description of Related Art

Periodontitis is an inflammatory reaction of the gingival tissues surrounding a tooth (periodontium) of a human or other toothed animal characterized by the formation of periodontal pockets (spaces) between the gum and tooth resulting in the loss of supporting bone due to the inflammatory process. The pockets accumulate bacteria, food, and other debris which wedge between teeth, especially if the gums have receded. Such accumulations manifest their presence by becoming calcified and adhere to the tooth structure.

Periodontal therapy when pocket formation has occurred often includes surgical removal of the diseased gingival tissues and recontouring of diseased areas utilizing a curette to produce an exposed environment where calcific deposits cannot collect or gather, and that are accessible to cleaning. Essentially what is necessary is removal of granulation tissue as well as inflamed gingival tissue residing in the periodontal pocket formed by surrounding healthy bone tissue and tooth.

Curettes have traditionally been used in dentistry to remove supragingival and subgingival dental deposits, to smooth root surfaces (root plane), to remove the soft tissue lining of a periodontal pocket (gingival curettage) and to fine scale and smooth tooth surfaces after the use of other scalers. Curettes generally possess a spoon-shaped blade with a continuous cutting edge forming a rounded tip, with the face and lateral sides meeting to form the cutting edge.

Curettes are currently available having two basic blade designs, i.e universal and specific. A universal curette is an instrument designed to adapt to most areas of the dentition, by modifying hand and finger positioning. The blade of a universal curette is generally characterized by two parallel cutting edges that form a rounded tip. Specific curettes are those adapted to specific anatomic areas of the teeth with only one lateral cutting edge used for instrumentation. Blade curvature and shank angulation limit the use of each specific curette to particular tooth surfaces.

The cutting and spooning action employed in periodontal curettage manually separates and removes the diseased granulation tissue or inflamed periodontal tissues from healthy bone tissue. In periodontal curettage, it is important that healthy gingival and bone tissue not be cut away because preservation of as much of these healthy tissues as possible is important for firm tooth support.

The cutting and spooning action of the periodontist using a curette is not only tedious and strenuous because of the physical effort required in separating the sinewy diseased and healthy tissues, but also awkward due to the multiple angles of manual movement of the curette necessary around the tooth and the restricted accessibility to periodontal pockets due to overall size, configuration, and functional limitations of the mouth structure.

These constraints, including blade and shank angulation, make manual positioning and movement of the curette extremely difficult to reach, scrape, cut, spoon, and remove debris from the bottom areas of deep periodontal pockets using prior art instruments. Not only are the angles, curvatures and direction of the actual curette blade important to the procedure, but also the length and angulation of the blade-bearing distal portion compared to the longitudinal axis of the gripping area of the instrument affects the ability of the practitioner to perform side-to-side directional cutting and spooning deep within deep periodontal pockets.

Horizontal rather than longitudinal angulation of the curette disclosed in U.S. Pat. No. 5,682,665 issued to Svanberg, does not allow for full side-to-side and up and down cutting within the deep pockets.

In U.S. Pat. No. 5,169,314 issued to Long, the right angle configuration of the curette blade portion compared to the distal portion of the shank limits cutting direction and accessibility particularly within deep periodontal pockets.

U.S. Pat. No. 4,505,678 issued to Andersson discloses an acute angle of the distal portion, however, the sharp cutting edges are angularly positioned within an opening at the rounded terminal end. Due to the opening and non-curved arrangement, the curette fails to provide an adequate means by which to cut and scoop out the undesirable debris from the pocket.

It is also important that the cutting portion of the instrument not have square edges, such as disclosed in U.S. Pat. No. 1,605,321 issued to Bates and U.S. Pat. Nos. 2,552,134 and 2,818,647 both issued to Berliner, as those configurations would gouge or cut into the roots of adjacent teeth or softer bony tissue. A rounded configuration allows the blade to adapt well to tooth surfaces and minimizes tissue trauma.

Curettes are generally comprised of an elongated, rigid, thin cylindrical or octagonal-shaped body having a roughened surface area for grasping manually with the thumb, middle and index fingers and have a curved cutting blade at the distal end of a shank, and secured to one or both ends of the instrument such as is disclosed in U.S. Pat. No. 5,682,665 issued to Svanberg. Projecting from one end of the instrument body is a thin, cylindrical shank. The shank may be angled in relation to the longitudinal axis of the instrument body for positioning and manipulation purposes within the mouth. The entire instrument is usually constructed of a single piece of durable metal. The exterior surface area for grasping is configured with patterns of grooves to increase the friction and manual grip ability when holding the curette during the scaling and root planing procedures.

Curettes are characteristically used in vertical, horizontal, or oblique directions; however, due to the small space and multiple confined angles within the mouth, it is often difficult to access and optimally position the cutting edges of the curette blade within deep periodontal pockets surrounding the tooth with maximum efficiency and minimal trauma to otherwise healthy tissues.

The invention described herein has been found to greatly increase access, efficiency and ability of the dental practitioner to properly and completely perform periodontal curettage particularly within deep pockets. The invention provides a curette with a blade face planar surface substantially parallel to the connection shank longitudinal axis, enabling efficient curette blade access to and separation of diseased granulation tissue lining the pocket wall from surrounding healthy bone tissue or in between or surrounding adjacent teeth in a periodontal cavity. The rounded tip and substantially parallel configuration of the blade face surface relative to the longitudinal axis of the distal portion of the shank and the about 90 degree angle between the distal and proximal portions of the shank enhance accessibility, ease of manipulation, directional cutting and efficiency of the procedure of voiding particularly deep periodontal pockets minimizing trauma or injury to healthy tissue. Because of the above orientation, the instrument can be manipulated easily. along the base of a deep pocket in a given direction.

BRIEF SUMMARY OF THE INVENTION

An apparatus for periodontal curettage including separating and removing diseased granulation tissue from healthy tissue in a periodontal pocket or cavity is provided. The invention is a rigid, elongated, thin cylindrical or octogonally-shaped body with at least one proximal shank and a distal shank having a spoon-shaped, rounded tip blade at the terminal end. The spoon-shaped blade face is less than or equal to 1.2 mm in width. The planar surface of the blade face is substantially parallel to and coaxial with the longitudinal axis of the distal shank. Although the blade face is parallel to the longitudinal axis of the blade and distal shank, the blade face orientation circumferentially around the distal shank can be in any direction and is selected based on the directional relationship of the shaft (handle), proximal and distal shanks and desired cutting direction. Four different blade face orientations, 90° apart on four different curettes can allow cutting and spooning motion in a deep tissue pocket in four desired directions, i.e., left to right, right to left, front to back, and back to front.

The configuration of the distal shank portion of the curette is preferably at about a ninety-degree angle to the proximal shaft portion and of sufficient length to enhance accessibility of the curette tips to the depth extremes of highly diseased periodontal pockets.

Instruments can be constructed in multiple embodiments wherein the spoon-shaped blade faces of the curettes are oriented substantially parallel and coaxial with, and rotated at 90 degree increments about the distal shank for specific manual, directional movement of the blade within a diseased pocket, allowing the periodontist to choose a specific blade face orientation for a specific direction of cutting and spooning in a particular pocket, i.e., left to right, right to left, front to back, and back to front.

It is the object of this invention to provide a hand-held curette that increases the manual efficiency, accessibility, visibility, and maneuverability while performing periodontal curettage, particularly in deep infra bony pockets, expand directional scraping and curetting abilities without increasing trauma or excessive removal of surrounding healthy bone tissue.

In accordance with this object and others which will become apparent hereinafter, the instant invention will now be described with particular reference to the accompanying drawings.

BRIEF DESCRIPTION OF THE SEVERAL VIEWS OF THE DRAWINGS

FIG. 3A is a side elevation view of an alternate embodiment.

FIG. 3B is a side elevation of a second double-ended embodiment.

PREFERRED EMBODIMENT OF THE INVENTION

Figure 1A:
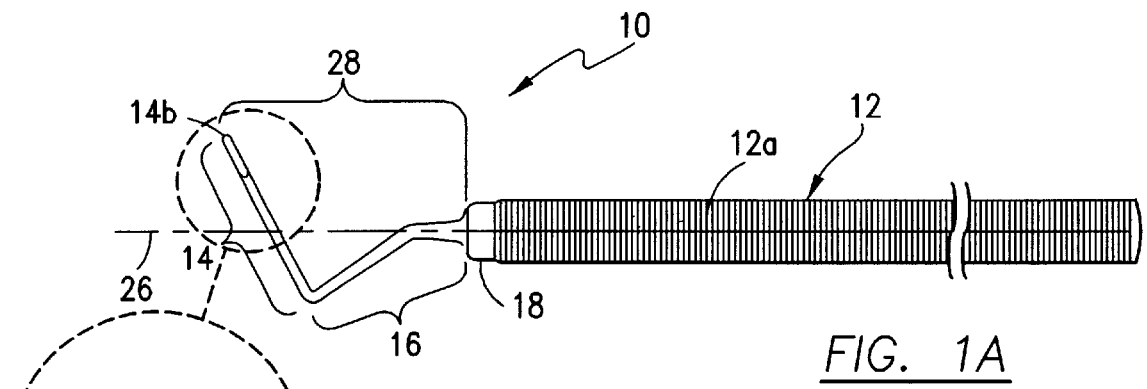
FIG. 1A is a side elevational view of the preferred embodiment of the invention.

Referring now to the drawings, and in particular, FIG. 1A, the invention is shown generally at 10, incorporated onto a surgical instrument, having an elongated, rigid cylindrical shaft 12 having a longitudinal axis 26 and terminating at shaft end 18. Shank 28 extends from the shaft end 18. Shank 28 further comprises a proximal shank portion 16 and a distal shank portion 14 terminating in a spoon-shaped blade 14a used in periodontal. surgical curettage. The proximal portion 16 is attached to the rigid cylindrical shaft surface area 12a that functions as a manual grasping handle. The shaft surface area 12a may be irregularly formed by grooves, ridges, or other friction or grip enhancing texture for better manual grasping.

Thus, as seen in FIG. 1A, the distal portion 14 is preferably configured at about a 90 degree angle to the proximal portion 16 for maximum angular maneuverability around the perimeter of the tooth and between the gum and tooth. Other angular configurations substantially less or substantially greater than 90 degrees may be used, however, maneuverability efficiency and accessibility will likely be diminshed.

Figure 1B:
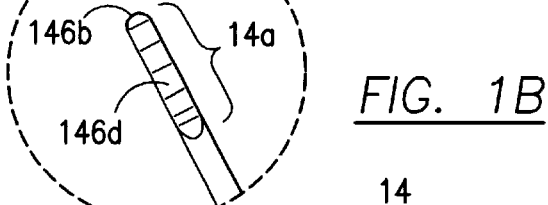
FIG. 1B is an enlarged fragmentary, top plan view of the curette spoon-shaped blade utilized in the invention.
Figure 1C:
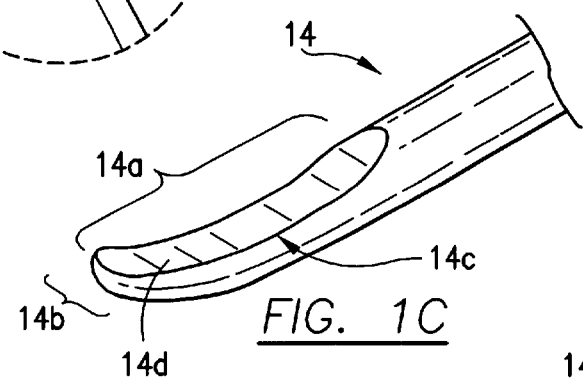
FIG. 1C is an enlarged perspective fragmentary view of the curette spoon shaped blade.
Figure 1D:
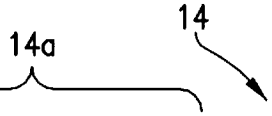
FIG. 1D is a side elevational view of the curette blade located at the terminal end of the distal portion of the shank as shown in FIGS. 1B and 1C.

FIGS. 1B, 1C, and 1D show enlarged views of the blade 14a of the distal portion 14 of the shank 28. Longitudinal, continuous sharp blade edges 14c extend back away from the rounded end tip 14b to form the interior blade surface 14d. The exterior surface of the curette blade face is somewhat elliptical, rounded and spoon-shaped in appearance. The blade face 14d is substantially parallel to .the longitudinal. axis of shank portion 14, allowing for penetration into deep pockets for right to left, left to right, front to back, and back to front movement of the blade 14d within different disposed pockets.

Figure 2A:
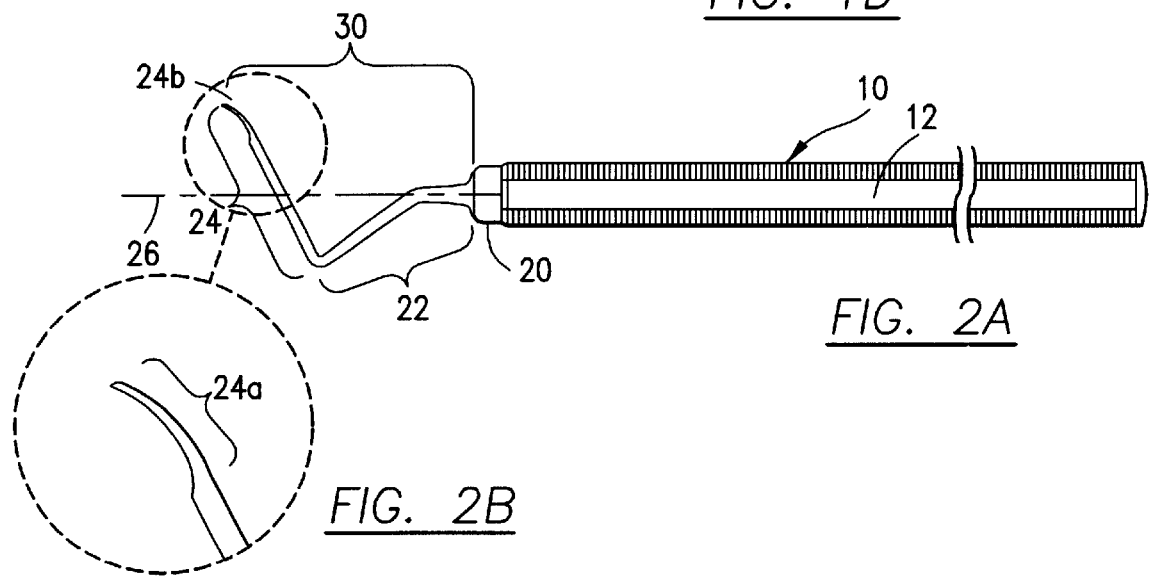
FIG. 2A is a side elevational view of the invention with the spoon-shaped blade oriented 90 degrees from the blade shown in FIG. 1A.
Figure 2B:
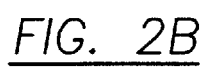
FIG. 2B is an enlarged side elevation view of the curette blade shown in FIG. 2A.

FIGS. 2A and 2B shows the blade 24a rotated 90 degrees about the longitudinal axis of the distal portion 24 as compared to the position of the blade 14a at the terminal end of distal portion 14 shown in FIG. 1A.

The instrument may have two functional curette ends located at opposite ends of the shank (handle) as shown in FIGS. 3A and 3B. The shank portion 30 at the end 20 of shaft 12 is likewise provided with a proximal portion 22 and a distal portion 24 terminating in a cutting spoon-shaped blade 24a. The blade face 24a is situated at the terminal end of the distal portion 24 at opposite shank end portion 30 to provide for cutting and spooning in two opposing directions, such as forward and backward in a deep periodontal pocket.

Thus, a single instrument can have two differently oriented spoon-shaped blade faces, one at each end, oriented 180 degrees apart to cut and spoon in opposing directions. Theoretically, the blade faces 14a and 24a may be rotated in one degree increments forming 360 different instruments circunmferentially relative to the shaft; however, it is believed that four instruments, each having orientations 90 degrees apart, are quite sufficient and useful for the majority of pocket cleaning. Each cutting direction can use a blade faces 14a and 24a of a different circumferential direction relative to the shaft 12.

The spatial orientation of the curette blade face around the longitudinal axis 26 may be in any direction, however, it is believed that 90 degree increments are sufficient for four different directions of cutting and spooning to provide the increased maneuverability and cutting accessibility necessary. Modifying hand and finger positioning during the cutting process provides almost an unlimited number of angulated cutting options.

Figure 4:
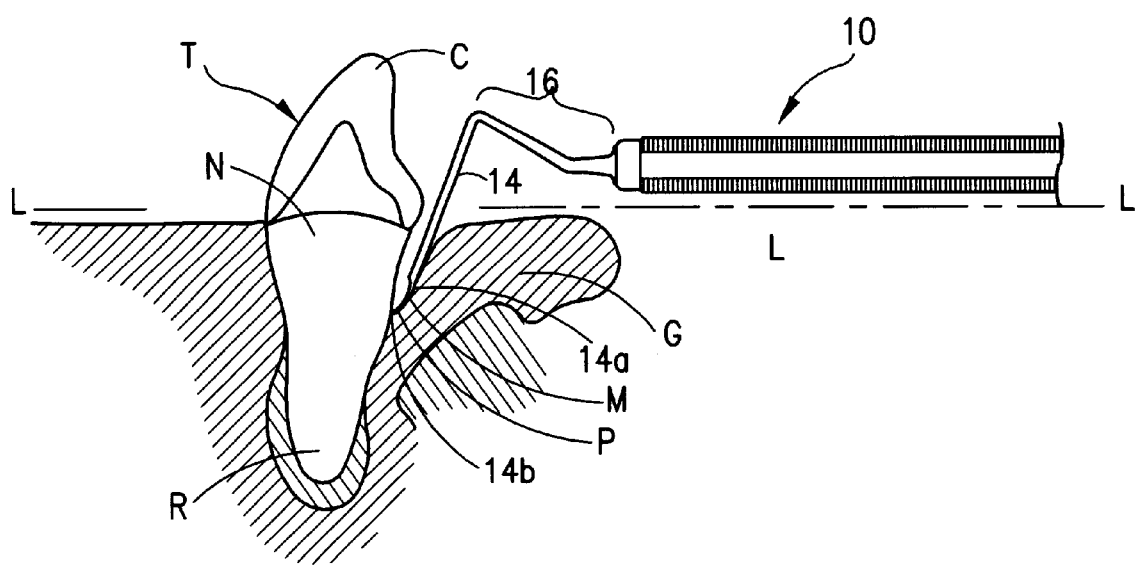
FIG. 4 is a side elevation cross sectional view of a jaw region showing a tooth with adhering calculus mass undergoing periodontal treatment with the present invention.

In FIG. 4 a typical tooth structure T is shown having crown C, neck N in the region of the gingival line L—L, and root R which extends down through gum G. Debris, granulation tissue and calculus mass M may be found deep within the pathologic pocket P formed in the subgingival region opposite the jaw alveolar bone J and adhering to the root surface. The dental instrument constructed to embody the invention is shown in use within the periodontal pocket P in proximity to the debris and calculus mass M within the pocket and adhering to root surface R of the tooth T. Proximal portion 16 is at about a right angle to distal portion 14 is inserted within the pocket with curette 14a along side of the debris mass M and curette tip 14b at the bottom of the pocket. The slight curvature of the curette blade face 14d provides debris scooping ability. In this example, the blade face 14d is facing the viewer and cutting action would be from back to front, toward the viewer. If the blade faced backwards (180° rotated), the cutting action would be front to back.

In operation, the curette blade face orientation relative to the handle and shank is selected for a desired direction then disposed in the periodontal pocket and the area scraped and spooned as described above, removing diseased granulation tissue and calculus along the bottom and sides of the pocket. Manual movement is directed in a single straight movement.

The instrument is constructed preferably of corrosion resistant metal, or other suitable material of sufficient strength, durability and flexibility to adequately perform the customary tasks associated with periodontal curettage as known in the art.

The invention has been found to greatly enhance the overall efficiency, visibility, accessibility and the ability to perform right to left, left to right, front to back, and back to front with four instruments, depending on blade face orientation, and cutting maneuvers with the curette within the pocket thereby facilitating the process of separating diseased tissue from the bone tissue and expediting periodontal surgical process.

These curettes can also be used for endodontic perioapical surgery.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An instrument for separating and voiding a diseased periodontal cavity of calculus and granulation tissue in a patient, comprising:

an elongated, rigid shaft having first and second ends, said first end terminating in a first distal portion which is connected to said rigid shaft by a first proximal portion at about a predetermined angle;

said first distal portion terminating in a first spoon-shaped blade having a first rounded end blade tip, and first spoon-shaped blade having a blade face, said first blade face having lateral sides which meet to form a continuous, sharp longitudinal cutting edge extending around said first rounded end blade tip, said first spoon-shaped blade having a face substantially parallel to the longitudinal axis of said first distal portion, and sized for insertion into a patient's mouth in the proximity of said diseased cavity so that calculus, debris, and granulation tissue may be cut, separated and removed; and said second distal portion terminating in a second spoon-shaped blade having a second rounded end blade tip, and second spoon-shaped blade interior surface, said second interior surface having lateral sides which meet to form a continuous, sharp longitudinal cutting edge extending around said second rounded end blade tip, said second spoon-shaped blade having a face substantially parallel to the longitudinal axis of the second distal portion and rotated 90 degrees from said first blade face, and sized for insertion into a patient's mouth in the proximity of said diseased cavity so that calculus, debris, and granulation tissue may be cut, separated and removed.

* * * * *